United States Patent [19]

Son et al.

[11] Patent Number: 4,692,487

[45] Date of Patent: Sep. 8, 1987

[54] 1,2-ETHANEDIYL-BIS-2-PIPERAZINONE ESTERS, OLIGOMERS THEREOF, AND COMPOSITIONS STABILIZED THEREBY

[75] Inventors: Pyong-Nae Son, Akron; John T. Lai, Broadview Heights, both of Ohio

[73] Assignee: The B. F. Goodrich Company, Akron, Ohio

[21] Appl. No.: 902,541

[22] Filed: Sep. 2, 1986

Related U.S. Application Data

[63] Continuation-in-part of Ser. No. 696,123, Jan. 29, 1985, abandoned.

[51] Int. Cl.$^4$ ................................................ C08K 5/34
[52] U.S. Cl. .................................. 524/100; 544/231; 544/358; 544/384
[58] Field of Search ................. 524/100; 544/231, 358, 544/384

[56] References Cited

U.S. PATENT DOCUMENTS

| | | | |
|---|---|---|---|
| 3,899,491 | 8/1975 | Ramey et al. | 524/100 |
| 4,097,452 | 6/1978 | Mayer et al. | 524/100 |
| 4,190,571 | 2/1980 | Lai et al. | 544/384 |
| 4,240,961 | 12/1980 | Lai | 544/384 |
| 4,455,401 | 6/1984 | Son et al. | 544/384 |
| 4,466,916 | 8/1984 | Lai et al. | 544/231 |
| 4,477,665 | 10/1984 | Lai et al. | 544/384 |
| 4,536,564 | 8/1985 | Woo | 544/384 |

Primary Examiner—John Kight
Assistant Examiner—Kriellion Morgan
Attorney, Agent, or Firm—Alfred D. Lobo; Alan A. Csontos

[57] ABSTRACT

A bis-polysubstituted piperazinone ("bis-PSP") in which two PSP moieties are closely coupled through an ethylene linkage, may be esterified so as to incorporate particular moieties in a macromolecule which may have only one bis-PSP unit, or may be esterified to form an oligomer having plural esterified bis-PSP repeating units. The macromolecule not only exhibits excellent UV-stabilization and antioxidant properties in synthetic resinous materials thus performing a highly effective dual function, but also is resistant to extraction with solvents, particularly polar solvents.

8 Claims, No Drawings

1,2-ETHANEDIYL-BIS-2-PIPERAZINONE ESTERS, OLIGOMERS THEREOF, AND COMPOSITIONS STABILIZED THEREBY

CROSS REFERENCE TO RELATED APPLICATION

This application is a continuation-in-part of Ser. No. 696,123, filed Jan. 29, 1985, now abandoned.

BACKGROUND OF THE INVENTION

This invention is related to a dual function stabilizer for organic materials, whether natural or synthetic, which are to be protected against degradation both by ultraviolet ("UV") light and oxygen, hence termed "dual-function". More specifically, the invention is related to an antioxidant ("AO") and UV-stabilizer ("UV-S") the dual function of which is attributable to the combination of a 1,2-ethanediyl-bis-($N^4$-polysubstituted-2-piperazinone) UV-stabilizing moiety and an ester moiety which contributes a surprising level of AO activity even when the ester does not include a hindered phenol (which one would expect to contribute such activity). The term "polysubstituted" refers specifically to a N-containing heterocyclic ring compound such as piperidine, piperazine, or 2-piperazinone in which at least the N-adjacent carbon atoms in the ring are each dialkyl-substituted, or one of the #3 or #5 C atoms, or each of them, is shared by a spiro cycloalkylene substituent. Such polysubstituted compounds belong to a class of compounds referred to as hindered amines which are known to be particularly useful as UV-S compounds in synthetic resinous materials.

As is well known, though numerous AOs and UV-Ss provide a significant measure of protection against degradation due to heat, very few UV-Ss provide appreciable protection against degradation due to oxygen. In particular, the clear instruction for the use of N-containing heterocyclic ring compounds having UV-S activity, is that they be used in admixture with AOs to provide the desired dual function.

For example, U.S. Pat. Nos. 4,167,512 and 4,190,571 to Lai et al disclose that a polysubstituted 2-piperazinone ("PSP") is an excellent UV-S, but teach that an AO be mixed with it to provide an organic material with protection, both against u-v light and oxidation. U.S. Pat. No. 3,899,491 to Ramey et al discloses a polysubstituted piperazine which is esterified with a short chain fatty acid ester (acetate, say) through the $N^1$ position which is not hindered. With this esterified piperazine, they teach that it is desirable to incorporate into the resin composition, sufficient thermal antioxidants to protect the plastic against thermal and oxidative degradation, and they specify a wide spectrum of phenolic antioxidants suitable for the purpose.

In our U.S. Pat. No. 4,477,665 we taught that a dual function stabilizer can be formed by esterifying an alkanol substituent on the $N^1$ atom of the PSP ring with a carboxylic acid functional hindered phenol, so as to leave a terminal hindered phenol group. Ignoring the fact that the alkanol substituent is on the unhindered $N^1$ atom in the '665 PSP, it is found that an analogous reaction does not proceed very satisfactorily with a hydroxyalkyl substituent on the hindered $N^4$ atom. The ester interchange does. This appears to be a peculiarity of the closely coupled PSP moieties in the bis-PSP compound, which of course, the '665 PSP is not.

Thus, the prior art simply failed to teach the desirability of providing the N-heterocyclic rings of a closely coupled bis-PSP with a hindered phenol terminal group in an ester substituent. Nor did it teach providing the bis-PSP with a long chain fatty acid ester. Most of all, there is no suggestion that this be done through the hindered $N^4$ position, which is what we have done.

Further, the esterification of a piperazine compound, such as is disclosed in the '491 patent, or a piperidine, is comparatively easy because of its relatively basic nature. By comparison, the esterification of a PSP is not, because the carbonyl (2-one) group in the ring renders it far less basic. Ignoring for the moment, the immediately evident resistance to substitution of the hindered $N^4$ position, the concept of esterifying the PSP through its hindered $N^4$ position would not appear readily to be translated into reality. The added complication of esterifying the bis-2-piperazinone compound in which two PSP moieties are closely coupled, thrust the concept even further from ready doability.

Referring further to the '571 patent, it teaches that 1,1'-(1,2-ethanediyl)bis[3,3,5,5-tetramethyl-2-piperazinone] is an excellent UV-S and that the $N^4$ position of each ring may be hydroxyethylated. Though the u-v stabilization ("UV-S") effectiveness of this bis-compound is not vitiated by hydroxyethylation, the presence of hydroxy groups is generally deemed undesirable because they render the UV-S solvent-extractable, and specifically, water-extractable. For many applications where resistance to extraction with water is not a factor, less than excellent resistance of the hydroxyethylated bis-compound is not a significant drawback; in still other instances, the separate addition of an antioxidant is undesirable. In those instances where water extraction is a factor, and a phenolic antioxidant is difficultly incorporated into the polymer to be stabilized, the foregoing drawbacks become critical.

The concept of coupling a nitrogen-containing heterocyclic ring compound with anything, whether a known heat stabilizer or an AO, in the same molecule, through either N-atom of the piperazine ring was out of favor, as is evident from the teachings of U.S. Pat. No. 4,097,452 to Mayer et al who taught that protection against both heat (not oxygen) and light degradation was better provided by spiro substituents.

In fact, the necessity of combining the UV-S and AO moieties for their respective activities arose through the common happenstance, for one reason or another, of dissatisfacation with stabilized polymers containing an admixture of UV-S and AO. One reason is that the UV-S and AO do not get essentially homogeneously dispersed in the polymer, with the result that one typically bleeds to the surface. For another, the interaction of separate UV-S and AO compounds in a mixture subjected to thermoforming conditions is difficult to predict.

Thus, many polysubstituted piperazinones have a significant level of UV-S activity, but each has one or more drawbacks which makes the one less desirable from a practical and utilitarian point of view, than another having a less objectionable drawback. This reality dictates the unending search, even in the narrow field of piperazinone-based stabilizers, for compounds with better UV-S activity, and results in discarding numerous stabilizers which do not have commercially significant activity.

Having found that we could esterify the $N^4$ hydroxylated bis-PSP by an ester interchange reaction so as to leave terminal hindered phenol groups on a hindered substituent to generate a macromolecule of bis-PSP, referred to herein as "the esterified bis-PSP", we found that some polymers stabilized with the esterified bis-PSP were prone to gas fade. Gas fade is evidence of sensitivity to nitrogen oxides present in the atmosphere and results in yellowing of the polymer, which in many instances, is unacceptable.

Moreover, the presence of the terminal hindered phenol groups greatly increased the polarity of the macromolecule so that its likelihood of being resistant to extraction with polar solvents such as water, was expected not to be high. As is well known, highly polar compounds dissolve in highly polar solvents (see *Organic Chemistry* by Morrison and Boyd, pg 31, 3rd ed, Allyn & Bacon, Inc. Boston). We were surprised to find the resistance to water extraction of the esterified bis-PSP from a synthetic resin such as polypropylene, was excellent. But the problem of gas fade persisted. So it was that we sought to substitute the hindered phenol with another moiety which did not subject the macromolecule to gas fade, was able to inculcate it with AO activity, yet have excellent resistance to extraction with solvents, particularly water.

It was in the foregoing factual framework that a solution was discovered to the problem of combining a single bis-PSP moiety having known UV-S activity, with an ester of a hindered phenol known to provide desirable dual function UV-S and AO activity; and, generating a macromolecule with plural repeating units of the bis-PSP esters of other moieties not known to provide AO activity, in such a way that they provide the dual function activity which resists extraction with hot water.

In particular, since there was nothing to suggest that a long chain fatty acid might contribute any AO activity to the bis-PSP macromolecule, we concluded it was unlikely to do so, yet be resistant to solvent extraction with solvents. We made the bis-PSP long chain fatty acid ester terminated macromolecule nevertheless, and happily discovered we were wrong. Moreover, the polarity of the macromolecule did not seem to contribute much to extractability, provided there was sufficient length to the macromolecule. This requirement of length, led to the synthesis of dual function bis-PSP oligomers having plural esterified bis-PSP repeating units, referred to herein as "esterified bis-PSP oligomers", by ester interchange. We found that a variety of ester moieties alternating with the bis-PSP in the esterified bis-PSP oligomers show desirable dual function activity.

SUMMARY OF THE INVENTION

It has been discovered that a known UV-S bis-PSP compound in which the PSP moieties are closely coupled through an ethylene linkage, may be esterified so as to incorporate particular moieties in a macromolecule referred to herein as "the esterified bis-PSP" because it has a single bis-PSP moiety. A macromolecule may also be generated by esterification to form an oligomer, referred to herein as "esterified bis-PSP oligomer" having plural esterified bis-PSP repeating units. The UV-S and AO activity of the macromolecule is such that it not only is a highly effective dual function stabilizer, but also is resistant to extraction with solvents, particularly polar solvents.

More specifically it has been discovered that a hydroxyalkylated bis-PSP compound in which the hydroxyalkyl substituent is on the hindered $N^4$ position of the PSP ring, may nevertheless be transesterified to provide a macromolecule with ester chain ends, so that the macromolecule, whether the esterified bis-PSP, or the esterified bis-PSP oligomer, performs as a dual function stabilizer resistant to extraction with water.

It is therefore a specific object of this invention to provide the esterified bis-PSP with dual UV-S and AO activity, in which the PSP moieties are closely coupled through their unhindered $N^1$ positions with an ethylene bridge, and which are esterified so that their hindered $N^4$ positions terminate with a hindered phenol or a long chain fatty acid having from 8 to about 20 carbon atoms.

It is also a general object of this invention to provide a stabilized synthetic resinous material containing an effective amount, sufficient to provide the desired level of protection against degradation by UV light and oxygen, of the aforedescribed esterified bis-PSP, or an esterified bis-PSP oligomer, each of which includes a bis-PSP closely coupled through an ethylene bridge, which peculiar structure is hypothesized to provide the macromolecule with excellent resistance to extraction with solvents.

DETAILED DESCRIPTION OF PREFERRED EMBODIMENTS

One preferred embodiment of the invention is the "esterified bis-PSP" in which the dual function UV-S and AO activity is attributable to the combination within the same macromolecule of closely coupled bis-PSP moieties, and terminal ester chain ends in which the terminal group is selected from a hindered phenol and a long chain fatty acid having from 8 to 20 carbon atoms.

The esterified bis-PSP is represented as follows:

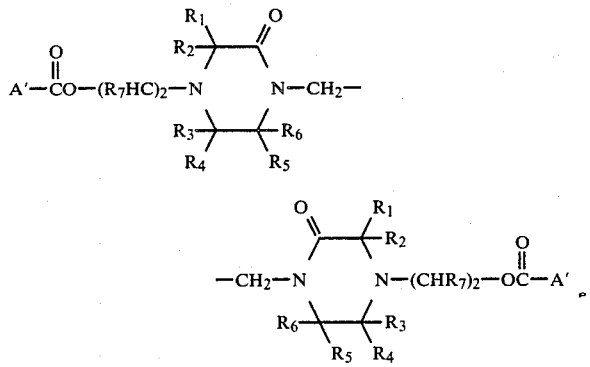

wherein,
A' represents
$CH_3-(CH_2)_x-$ wherein x is an integer in the range from 6 to about 20; and,
hydroxyphenyl having $C_1-C_{10}$ alkyl substituents;
$R_1-R_4$ each independently represent $C_1-C_{12}$ alkyl; $C_5-C_{14}$ cycloalkyl or hydroxycycloalkyl having from 5 to 8 ring C atoms, $C_7-C_{14}$ alkenyl or aralkyl; $C_2-C_7$ alkylene;
$R_1$ and $R_2$, or $R_3$ and $R_4$ together with the ring C atom of the piperazinone ring represent cycloalkyl having from 5 to about 8 ring C atoms; and,
$R_5$ and $R_6$ are the same as $R_1-R_4$ defined above, and additionally may be H; and,
$R_7$ represents lower alkyl $C_1-C_6$, and H.

Preferably $R_1$–$R_4$ are lower alkyl, for example methyl, and $R_5$ and $R_6$ are H.

In another embodiment, the stabilizer is an "esterified bis-PSP oligomer" containing from 2 to about 10 esterified closely coupled bis-PSP repeating units, and may be represented as follows:

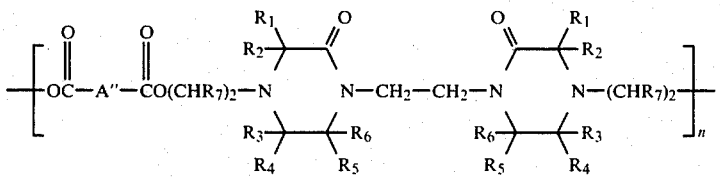

wherein n is an integer in the range from 2 to about 10; A'' represents alkylene —$(CH_2)_{n'}$— wherein n' is an integer in the range from 2 to about 20, and cycloalkylene (or cyclodiyl)

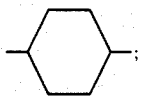

and, $R_7$ has the same connotation as that given hereinabove.

The "esterified bis-PSPs" and "esterified bis-PSP oligomers" range in physical form, at room temperature, from solids to liquids, and are soluble or partially soluble in common solvents such as acetone, diethyl ether, dioxane, tetrahydrofuran, carbon tetrachloride, chloroform, lower primary alcohols having from 1 to about 5 C atoms such as methanol, ethanol and propanol, aromatic hydrocarbons such as benzene and toluene, but much less soluble in aliphatic hydrocarbons such as hexane. Both the esterified bis-PSP and the esterified bis-PSP opligomers are generally insoluble in water. Many are white when pure.

Particular esterified bis-PSPs of this invention include
(i) 1,2-ethanediylbis[2,2,6,6-tetramethyl-2-oxo-4,1-piperazinediyl)-2,1-ethanediyl] ester of 3,5-bis(1,1-dimethylethyl)-4-hydroxybenzenepropanoic acid;
(ii) 1,2-ethanediylbis[2,2,6,6-tetramethyl-2-oxo-4,1-piperazinediyl)-2,1-ethanediyl] ester of stearic acid;
(iii) 1,2-ethanediylbis[2,2,6,6-tetramethyl-2-oxo-4,1-piperazinediyl)-1-methyl-2,1-ethanediyl] ester of 3,5-bis(1,1-dimethylethyl)-4-hydroxybenzene-propanoic acid; and,
(iv) 1,2-ethanediylbis[2,2,6,6-tetramethyl-2-oxo-4,1-piperazinediyl)-1-methyl-2,1-ethanediyl] ester of stearic acid.

Particular esterified bis-PSP oligomers of this invention include
(i) poly[oxycarbonyl-1,2-ethanediylcarbonyloxy-1,2-ethanediyl(2,2,6,6-tetramethyl-3-oxo-1,4-piperazinediyl)-1,2-ethanediyl(3,3,5,5-tetramethyl-2-oxo-1,4-piperazinediyl)1,2-ethanediyl];
(ii) poly[oxycarbonyl-1,8-octanediylcarbonyloxy-1,2-ethanediyl(2,2,6,6-tetramethyl-3-oxo-1,4-piperazinediyl)-1,2-ethanediyl(3,3,5,5-tetramethyl-2-oxo-1,4-piperazinediyl)1,2-ethanediyl];
(iii) poly[oxycarbonyl-1,3-propanediylcarbonyloxy-1,2-ethanediyl(2,2,6,6-tetramethyl-3-oxo-1,4-piperazinediyl)-1,2-ethanediyl(3,3,5,5-tetramethyl-2-oxo-1,4-piperazinediyl)1,2-ethanediyl]; and the like.

The novel compounds of this invention may be prepared by reaction of bis-PSP with the appropriate ester in the presence of an esterification catalyst. Particular bis-PSPs used are disclosed in U.S. Pat. No. 4,167,512, the disclosure of which is incorporated by reference thereto as if fully set forth herein. Appropriate esters include for example, methyl stearate, dimethyl succinate, dimethyl sebacate, dimethyl glutarate, ethyl 3,5-bis(1,1-dimethylethyl)-4-hydroxybenzenepropanoate, and the like. Effective stabilizers have a number average mol wt of at least about 400 and preferably less than 10,000.

Suitable catalysts include for example, organometallic compounds such as tetraisopropyl-orthotitanate and potassium tert-butoxide ("K—O—Bu"). The reaction may be carried out in the presence of inert solvents such as dichlorobenzene, chlorobenzene, hexane, toluene, xylene, and the like.

The amount of stabilizer employed will vary with the particular material to be stabilized and also the substituents used. Generally however, for effective UV stabilization of organic materials, an amount of the esterified bis-PSP or oligomer used is in the range from about 0.01% by wt to about 10% by wt, based on the wt of organic material. In typical stabilized polymers, and particularly in synthetic resinous materials, the amount of esterified bis-PSP or oligomer used is in the range from about 0.01 to about 5% by wt.

The pivotal characteristic of stabilized compositions of this invention is that they simultaneously combat the deleterious effects of uv light, thermal and oxidative degradation, such as are usually evidenced by discoloration and/or embrittlement, without the addition of secondary stabilizers. Thus, in the majority of instances where the dual-function stabilizers of this invention are used, no additional AO is necessary.

In a situation where even greater AO stability is desired than is generally deemed adequate, a compatible and essentially homogeneously dispersible secondary stabilizer is mixed into the continuous organic phase of the organic polymer to be stabilized. Therefore, in such a situation, in conjunction with the stabilizers of this invention, compositions may include a secondary stabilizer which may be present in the range from about 0.01 to about 10 phr, and preferably from about 0.1 to about 5 phr of the organic continuous phase. Such a secondary stabilizer may be one of several types of known secondary stabilizers for example, those disclosed in U.S. Pat. Nos. 3,325,448; 3,769,259; 3,920,659; 3,962,255; 3,966,711; 3,971,757; inter alia.

Organic materials which may be stabilized against uv light, thermal and oxidative degradation, include copolymers of butadiene with acrylic acid, alkyl acrylates or methacrylates, polyisoprene, polychloroprene, and the like; polyurethanes; vinyl polymers known as PVC resins such as polyvinyl chloride, copolymers of vinyl chloride with vinylidene chloride, copolymers of vinyl halide with butadiene, styrene, vinyl esters, and the like; polyamides such as those derived from the reaction of hexamethylene diamine with adipic or sebacic acid; epoxy resins such as those obtained from the condensation of epichlorohydrin with bisphenols, and the like; ABS resins, polystyrene, polyacrylonitrile, polymethacrylates, polycarbonates, varnish, phenol-formaldehyde resins, polyepoxides, polyesters, and polyolefin homo- and copolymers such as polyethylene, polypropylene, ethylene-propylene polymers, ethylene-propylenediene polymers, ethylene vinyl acetate polymers and the like. The esterified bis-PSP or oligomer may also be used to stabilize mixtures and blends of oligomeric materials such as ABS resin blends, PVC and polymethacrylate blends, and blends of homopolymers and copolymers such as blends of polypropylene in EPDM polymers.

Most particularly, the esterified bis-PSPs or oligomers are especially useful as uv-light stabilizers for synthetic resinous materials used in the form of fibers, or in thermoformed shapes which are at least partially permeable to visible light, and particularly for those which are transparent thereto, such as polyvinylaromatics and polyolefins.

Many known compounding ingredients may be used along with the esterified bis-PSP or oligomer in the compositions. Such ingredients include metal oxides such as zinc, calcium and magnesium oxide, fatty acids such as stearic and lauric acid, and salts thereof such as calcium, zinc and sodium stearate and lead oleate; fillers such as calcium and magnesium carbonate, calcium and barium sulfates, aluminum silicates, asbestos, and the like; plasticizers and extenders such as dialkyl and diaryl organic acids like diisobutyl, diisooctyl, diisodecyl, and dibenzyl oleates, stearates, sebacates, azelates, phthalates, and the like; ASTM type 2 petroleum oils, paraffinic oils, castor oil, tall oil, glycerin and the like.

Particularly desirable secondary stabilizers are one or more antioxidants used in the range from about 0.01 phr to about 20 phr, preferably from about 0.02 to about 5 phr of the material to be stabilized. Of the types of antioxidants used, are phosphite, phosphate, sulfide and phenolic antioxidants, the last being preferred. Most preferred are the hindered phenol AOs specified hereinabove, though others are also useful such as 2,6-di-t-butyl-paracresol; 2,2'-methylene-bis(6-t-butyl-phenol); 2,2'-thiobis(4-methyl-6-t-butyl-phenol); 2,2'-methylenebis(6-t-butyl-4-ethyl-phenol); 4,4'-butylidenebis(6-t-butyl-m-cresol); 2-(4-hydroxy-3,5-di-t-butylanilino)-4,6-bis(octylthio)-1,3,5-triazine; benzenepropanoic acid, 3,5-bis(1,1-dimethylethyl)-4-hydroxy-,(2,4,6-trioxo-1,3,5-triazine-1,3,5(2H,4H,6H)-triyl)tri-2,1-ethanediyl ester (Goodrite ® 3125); tetrakis[methylene 3-(3',5'-di-t-butyl-4'-hydroxyphenyl)propionate]methane; and particularly commercially available antioxidants such as Irganox 1010, 1035, 1076 and 1093, and Goodrite 3114. Other ingredients such as pigments, tackifiers, flame retardants, fungicides, and the like may also be added.

The esterified bis-PSP or oligomer, and other compounding ingredients if used, can be admixed with the material to be stabilized using known mixing techniques and equipment such as internal mixing kettles, a Banbury mixer, a Henschel mixer, a two-roll mill, an extruder mixer, or other standard equipment, to yield a composition which may be extruded, pressed, blow-molded or the like into film, fiber or shaped articles. Usual mixing times and temperatures can be employed which may be determined with a little trial and error for any particular composition. The objective is to obtain intimate and uniform mixing of the components. A favorable mixing procedure to use when adding the esterified bis-PSP to an organic material is either to dissolve or suspend the esterified bis-PSP or oligomer in a liquid such as methylene chloride before adding it, or to add the esterified bis-PSP directly to the oligomeric material whether the esterified bis-PSP is in the form of a powder or oil, or to extruder-mix the esterified bis-PSP and material prior to forming the product.

The UV-stability of a stabilized composition can be evaluated by exposing a prepared sample of the composition to Xenon or carbon arc light in a Weather-O-Meter (ASTM D2569-79) operating at a temperature of about 145° F. (63° C.) at about 50% relative humidity. Degradation of the sample is monitored by periodically measuring the tensile strength after exposure, and the hydroperoxide absorption band at 3460 cm$^{-1}$ or carbonyl absorption band at 1720 cm$^{-1}$ using an IR spectrophotometer. The rapid formation of carbonyl indicates failure of the sample. The test procedure is well known, and is published in the text *Photodegradation, Photooxidation and Photostabilization of Polymers* by Ranby and Rabek, John Wiley & Sons, N.Y., N.Y. (1975), at pg 129 et seq., and is disclosed in U.S. Pat. No. 3,909,493. Failure of the sample is also checked by visual signs of cracking when the sample is bent 180°.

Samples of the compositions are also checked for oxidative and thermal stability by measuring the time to discoloration and/or embrittlement of the sample after aging in an air circulating oven at 125° C. (ASTM D1204-78), and other standard tests. These tests include tests for resistance to extraction with boiling water for a period of 24 hr.

The invention is illustrated by the following examples for preparation of the esterified bis-PSPs and the oligomers.

EXAMPLE I

Preparation of
1,2-ethanediylbis[2,2,6,6-tetramethyl-2-oxo-4,1-piperazinediyl)-2,1-ethanediyl] ester of
3,5-bis(1,1-dimethylethyl)-4-hydroxybenzenepropanoic acid A 4-neck 150 ml flask is charged with 96.9 g of ethyl 3,5-bis(1,1-dimethylethyl)-4-hydroxybenzenepropanoate and heated to 140° C. while 33.7 g of 1,1'-(1,2-ethanediyl)bis[4-(2-hydroxyethyl)-3,3,5,5-tetramethylpiperazinone] are added. The mixture is further heated to 183° C. and 0.5 ml of tetra-isopropyl orthotitanate is added. After collecting about 8 ml of ethanol, the reaction temperature was maintained at about 180° C. for about 1 hr and the reaction then terminated. The resulting taffy-like reaction product was placed in 600 ml of hot hexane, and stirred for 5 min to yield a tan solid product which was washed with water to yield 66.5 g of dried crude product.

For analysis, a sample of the crude product was recrystallized from 1-pentanol followed by two additional recrystallizations from toluene. The product had a melting point of 174°–176.5° C. Field Desorption (FD) mass spectroscopic analysis indicates that the structure is as follows:

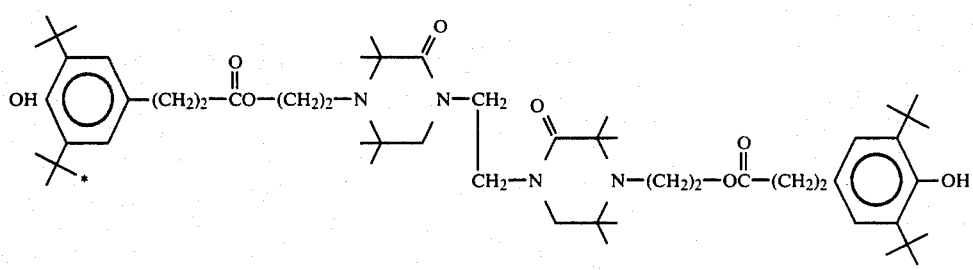

*line substituent = Methyl

EXAMPLE II

Preparation of 1,2-ethanediylbis[2,2,6,6-tetramethyl-2-oxo-4,1-piperazinediyl)-2,1-ethanediyl] ester of stearic acid In a manner generally analogous to that set forth in Example I hereinabove, 33.7 g of 1,1'-(1,2-ethanediyl)-bis[4-(2-hydroxyethyl)-3,3,5,5-tetramethylpiperazinone] are reacted with 94.4 g of methyl stearate to yield a crude product which was recrystallized from ethyl acetate and then from hexane-toluene. The product had a melting pt of 73°–76° C. and the following structure:

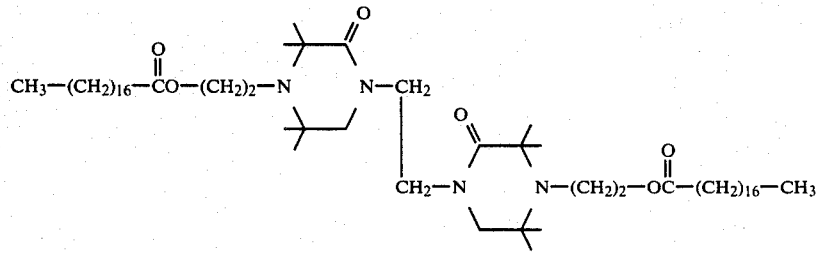

EXAMPLE III

Preparation of poly[oxycarbonyl-1,2-ethanediylcarbonyloxy-1,2-ethanediyl(2,2,6,6-tetramethyl-3-oxo-1,4-piperazinediyl)-1,2-ethanediyl(3,3,5,5-tetramethyl-2-oxo-1,4-piperazinediyl)1,2-ethanediyl].

A 3-neck 100 ml flask is charged with 10.66 g 1,1'-((1,2-ethanediyl)bis[4-(2-hydroxyethyl)-3,3,5,5-tetramethylpiperazinone], 4.02 g of dimethyl succinate, 50 ml of dichlorobenzene, and 1.0 g of K—O—Bu, and the mixture heated at 130°–140° C. for about 4 hr, then allowed to react overnight at 120° C., and the reaction terminated. The resulting thick syrup ws triturated in water, then dissolved in hot toluene. After stripping the toluene, a light yellow taffy-like product was recovered which was washed in hot hexane in which it was insoluble. The product had a number average mol wt (Mn) of 1870 and the structure

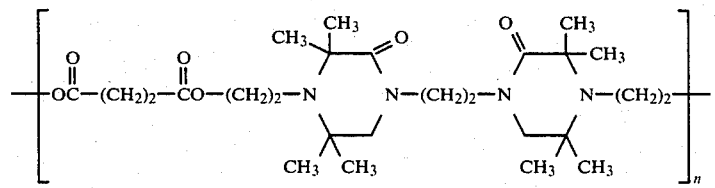

EXAMPLE IV

Preparation of (ii) poly[oxycarbonyl-1,8-octanediylcarbonyloxy-1,2-ethanediyl(2,2,6,6-tetramethyl-3-oxo-1,4-piperazinediyl)-1,2-ethanediyl(3,3,5,5-tetramethyl-2-oxo-1,4-piperazinediyl)1,2-ethanediyl]

In a manner generally analogous to that described in Example III hereinabove, the flask is charged with 14.9 g 1,1'-(1,2-ethanediyl)bis[4-(2-hydroxyethyl)-3,3,5,5-tetramethylpiperazinone], 7.8 g of dimethyl sebacate, 65 ml of dichlorobenzene, and 1.5 g of K-O-Bu, and the mixture reacted. The reaction product recovered was dissolved in 200 ml methylene chloride and washed with 200 ml water. The organic layer was separated, dried over sodium sulfate and stripped to isolate 12.4 g of resinous product. The product had a Mn of 1430 and the following structure:

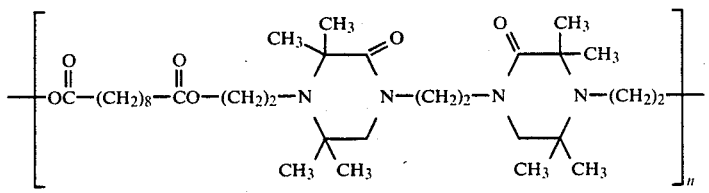

EXAMPLE V

Preparation of poly[oxycarbonyl-1,3-propanediylcarbonyloxy-1,2-ethanediyl(2,2,6,6-tetramethyl-3-oxo-1,4-piperazinediyl)-1,2-ethanediyl(3,3,5,5-tetramethyl-2-oxo-1,4-piperazinediyl)1,2-ethanediyl]

In a manner generally analogous to that described in Example III hereinabove, the flask is charged with 14.9 g 1,1′-(1,2-ethanediyl)bis[4-(2-hydroxyethyl)-3,3,5,5-tetramethylpiperazinone], 6.3 g of dimethyl glutarate, 65 ml of dichlorobenzene, and 1.5 g of K-O-Bu, and the mixture reacted. The reaction product recovered was dissolved in 200 ml methylene chloride and washed with 200 ml water. The organic layer was separated, dried over sodium sulfate and stripped to isolate 13.9 g of resinous product. The product had a Mn of 1260 and the following structure:

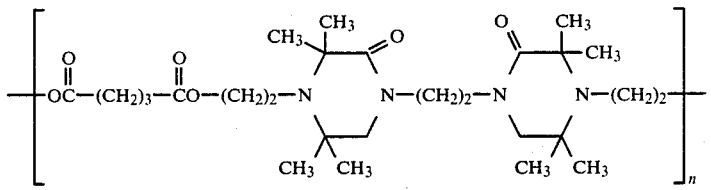

In the following Table is listed the results of a series of tests for the effectiveness of the foregoing specific compounds as dual function stabilizers. All compounds were tested at a level of 0.1 g per 100 g of Profax 6501 polypropylene tape, 2 mil thick. The control is a piece of 2 mil thick tape with no UV-S or AO additives. The sample designated "Lai 2G" is the stabilizer in Ex. 2G of the Lai U.S. Pat. No. 4,190,571. Tinuvin®770 is a comercially available stabilizer which is a substituted piperidyl hindered amine ester. Samples before water extraction are designated "Fresh", and, after water extraction with boiling water for 24 hr, are designated "Water extr.".

TABLE

| Sample | Xenon Weather-O-Meter (hr) | | Oven Aging (days) | |
|---|---|---|---|---|
| | Fresh | Water extr. | Fresh | Water extr. |
| Control | 240 | 160 | 2 | 1 |
| Lai 2G | 2400* | 390 | 2 | 2 |
| Tinuvin ® 770 | 2700* | 800 | 4 | 3 |
| Ex. I | 1680 | 1000* | 16 | 10* |
| Ex. II | 1100 | 1000* | 19 | 10* |
| Ex. IV | 1780 | 1590 | 18 | 7 |
| Ex. V | 2180 | 1700 | 13 | 7 |

*test discontinued

From the foregoing data it is evident that the Lai 2G bis compound (not esterified) has essentially no AO activity (same as the blank control). Though the Lai 2G bis compound has excellent UV-S activity before it is extracted with hot water, the activity drops off sharply after extraction, a characteristic similar to that of the Tinuvin 770.

We claim:

1. An esterified bis-polysubstituted piperazinone ("bis-PSP") represented by the structure

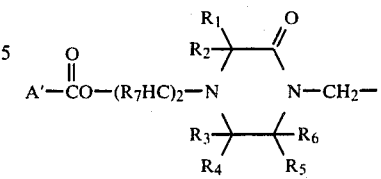

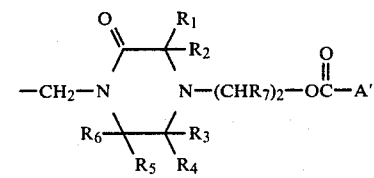

wherein,

A′ represents
$CH_3—(CH_2)_x—$ wherein x is an integer in the range from 6 to about 20; and,
hydroxyphenyl having $C_1-C_{10}$ alkyl substituents;

$R_1-R_4$ each independently represent $C_1-C_{12}$ alkyl; $C_5-C_{14}$ cycloalkyl or hydroxycycloalkyl having from 5 to 8 ring C atoms, $C_7-C_{14}$ alkenyl or aralkyl; $C_2-C_7$ alkylene;

$R_1$ and $R_2$, or $R_3$ and $R_4$ together with the ring C atom of the piperazinone ring represent cycloalkyl having from 5 to about 8 ring C atoms; and, $R_5$ and $R_6$ are the same as $R_1-R_4$ defined above, and additionally may be H; and, $R_7$ represents lower alkyl $C_1-C_6$, and H.

2. An esterified bis-polysubstituted piperazinone oligomer ("bis-PSP oligomer") having the structure

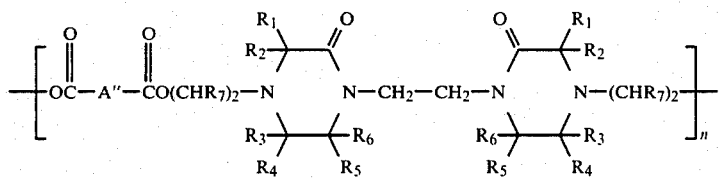

wherein,

A″ represents
- —$(CH_2)_{n'}$—, alkylene, wherein n′ is an integer in the range from 2 to about 20; and,
- cycloalkylene having 5 to about 8 ring carbon atoms;

$R_1$–$R_4$ each independently represent $C_1$–$C_{12}$ alkyl; $C_5$–$C_{14}$ cycloalkyl or hydroxycycloalkyl having from 5 to 8 ring C atoms, $C_7$–$C_{14}$ alkenyl or aralkyl; $C_2$–$C_7$ alkylene;

$R_1$ and $R_2$, or $R_3$ and $R_4$ together with the ring C atom of the piperazinone ring represent cycloalkyl having from 5 to about 8 ring C atoms; and, $R_5$ and $R_6$ are the same as $R_1$–$R_4$ defined above, and additionally may be H; and, $R_7$ represents lower alkyl $C_1$–$C_6$, and H.

3. The esterified bis-PSP of claim 1 represented by the structure

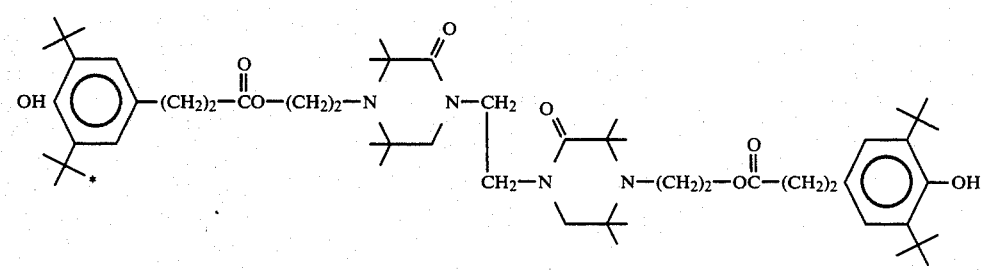

*line substituent = Methyl and identified as the 1,2-ethanediylbis[2,2,6,6-tetramethyl-2-oxo-4,1-piperazinediyl)-1-methyl-2,1-ethanediyl] ester of 3,5-bis(1,1-dimethylethyl)-4-hydroxybenzenepropanoic acid.

4. The esterified bis-PSP of claim 1 represented by the structure

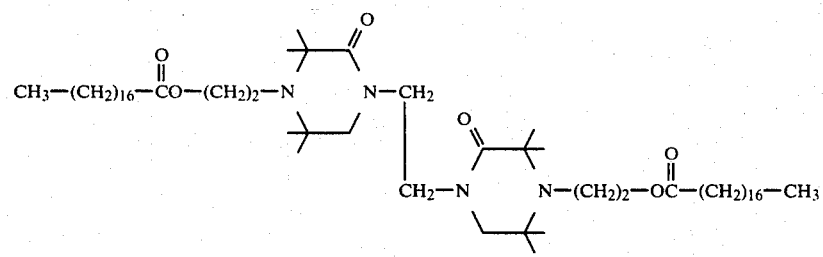

and identified as the 1,2-ethanediylbis[2,2,6,6-tetramethyl-2-oxo-4,1-piperazinediyl)-2,1-ethanediyl] ester of stearic acid.

5. The esterified bis-PSP oligomer of claim 2 represented by the structure

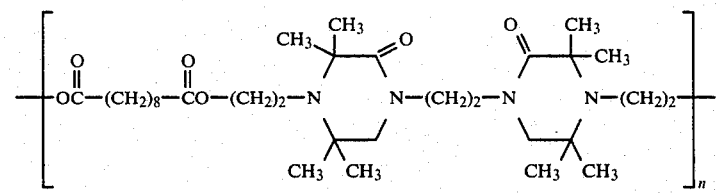

and identfied as (ii) poly[oxycarbonyl-1,8-octanediylcarbonyloxy-1,2-ethanediyl(2,2,6,6-tetramethyl-3-oxo-1,4-piperazinediyl)-1,2-ethanediyl(3,3,5,5-tetramethyl-2-oxo-1,4-piperazinediyl)1,2-ethanediyl].

6. The esterified bis-PSP oligomer of claim 2 represented by the structure

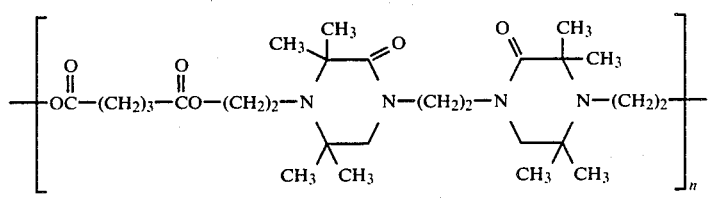

and identified as poly[oxycarbonyl-1,3-propanediylcarbonyloxy-1,2-ethanediyl(2,2,6,6-tetramethyl-3-oxo-1,4-piperazinediyl)-1,2-ethanediyl(3,3,5,5-tetramethyl-2-oxo-1,4-piperazinediyl)1,2-ethanediyl].

7. A stabilized composition of matter comprising an organic material subject to degradation by ultravilet light or ooxidation, having dispersed therein from about 0.02 part to about 5 parts by weight per 100 parts by weight of said organic material, a stabilizer selected from the group consisting of an esterified bis-polysubstituted piperazinone ("bis-PSP") represented by the structure

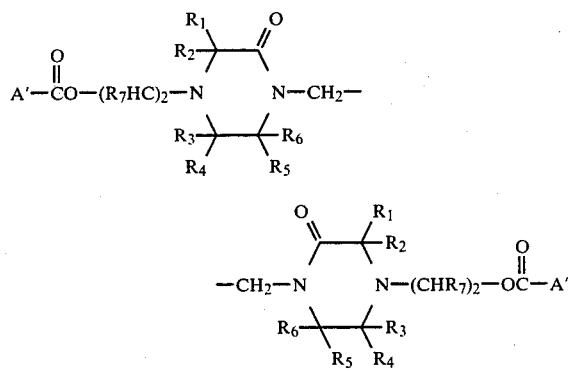

and, an esterified bis-polysubstituted piperazinone oligomer ("bis-PSP oligomer") represented by the structure

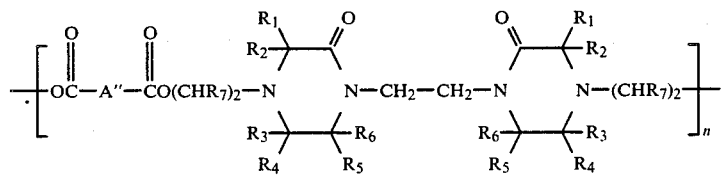

wherein,
A' represents
CH₃—(CH₂)$_x$— wherein x is an integer in the range from 6 to about 20; and,
hydroxyphenyl having $C_1$-$C_{10}$ alkyl substituents;
A" represents
—(CH₂)$_{n'}$—, alkylene, wherein n' is an integer in the range from 2 to about 20; and,
cycloalkylene having 5 to about 8 ring carbon atoms;
$R_1$-$R_4$ each independently represent $C_1$-$C_{12}$ alkyl; $C_5$-$C_{14}$ cycloalkyl or hydroxycycloalkyl having from 5 to 8 ring C atoms, $C_7$-$C_{14}$ alkenyl or aralkyl; $C_2$-$C_7$ alkylene;
$R_1$ and $R_2$, or $R_3$ and $R_4$ together with the ring C atom of the piperazinone ring represent cycloalkyl having from 5 to about 8 ring C atoms; and,
$R_5$ and $R_6$ are the same as $R_1$-$R_4$ defined above, and additionally may be H; and,
$R_7$ represents lower alkyl $C_1$-$C_6$, and H.
8. The stabilized composition of claim 7 wherein said esterified bis-PSP is selected from the group consisting of
(i) 1,2-ethanediylbis[2,2,6,6-tetramethyl-2-oxo-4,1-piperazinediyl)-2,1-ethanediyl] ester of 3,5-bis(1,1-dimethylethyl)-4-hydroxybenzenepropanoic acid;
(ii) 1,2-ethanediylbis[2,2,6,6-tetramethyl-2-oxo-4,1-piperazinediyl)-2,1-ethanediyl] ester of stearic acid;
(iii) 1,2-ethanediylbis[2,2,6,6-tetramethyl-2-oxo-4,1-piperazinediyl)-1-methyl-2,1-ethanediyl] ester of 3,5-bis(1,1-dimethylethyl)-4-hydroxybenzene-propanoic acid; and,
(iv) 1,2-ethanediylbis[2,2,6,6-tetramethyl-2-oxo-4,1-piperazinediyl)-1-methyl-2,1-ethanediyl] ester of stearic acid;
and, said esterified bis-PSP oligomer is selected from the group consisting of
(i) poly[oxycarbonyl-1,2-ethanediylcarbonyloxy-1,2-ethanediyl(2,2,6,6-tetramethyl-3-oxo-1,4-piperazinediyl)-1,2-ethanediyl(3,3,5,5-tetramethyl-2-oxo-1,4-piperazinediyl)1,2-ethanediyl];
(ii) poly[oxycarbonyl-1,8-octanediylcarbonyloxy-1,2-ethanediyl(2,2,6,6-tetramethyl-3-oxo-1,4-piperazinediyl)-1,2-ethanediyl(3,3,5,5-tetramethyl-2-oxo-1,4-piperazinediyl)1,2-ethanediyl]; and,
(iii) poly[oxycarbonyl-1,3-propanediylcarbonyloxy-1,2-ethanediyl(2,2,6,6-tetramethyl-3-oxo-1,4-piperazinediyl)-1,2-ethanediyl(3,3,5,5-tetramethyl-2-oxo-1,4-piperazinediyl)1,2-ethanediyl].

* * * * *